(12) United States Patent
Williams

(10) Patent No.: US 10,314,775 B2
(45) Date of Patent: Jun. 11, 2019

(54) METHODS OF INCREASING HAIR GROWTH AND IMPROVING HAIR APPEARANCE

(71) Applicant: MyMD Pharmaceuticals, Inc., Tampa, FL (US)

(72) Inventor: Jonnie R. Williams, Sarasota, FL (US)

(73) Assignee: MyMD Pharmacueticals, Inc., Tampa, FL (US)

( * ) Notice: Subject to any disclaimer, the term of this patent is extended or adjusted under 35 U.S.C. 154(b) by 0 days.

(21) Appl. No.: 15/998,646

(22) PCT Filed: Feb. 13, 2017

(86) PCT No.: PCT/US2017/017641
§ 371 (c)(1),
(2) Date: Aug. 16, 2018

(87) PCT Pub. No.: WO2017/142833
PCT Pub. Date: Aug. 24, 2017

(65) Prior Publication Data
US 2019/0133910 A1    May 9, 2019

Related U.S. Application Data

(60) Provisional application No. 62/295,618, filed on Feb. 16, 2016.

(51) Int. Cl.
| | |
|---|---|
| *A61K 8/49* | (2006.01) |
| *A61K 9/00* | (2006.01) |
| *A61K 31/4439* | (2006.01) |
| *A61Q 7/00* | (2006.01) |
| *A61Q 5/00* | (2006.01) |
| *A61P 17/14* | (2006.01) |

(52) U.S. Cl.
CPC .......... *A61K 8/4926* (2013.01); *A61K 9/0014* (2013.01); *A61K 9/0053* (2013.01); *A61K 31/4439* (2013.01); *A61P 17/14* (2018.01); *A61Q 5/00* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 6,448,276 B1 | 9/2002 | Yerxa | |
| 2012/0093752 A1* | 4/2012 | DiColandrea | A61K 8/40 424/70.1 |
| 2018/0271875 A1* | 9/2018 | Williams | A61P 37/02 |

FOREIGN PATENT DOCUMENTS

| | | |
|---|---|---|
| WO | 2016-161051 A1 | 10/2016 |
| WO | 2016-161055 A2 | 10/2016 |

OTHER PUBLICATIONS

International Search Report and Written Opinion for PCT/US2017/017641, dated May 22, 2017.
PubChem, SID 254779196 (Nov. 11, 2015) URL: http://pubchem.ncbi.nlm.nih.gov/substance/254779196.

* cited by examiner

*Primary Examiner* — Dennis Heyer
(74) *Attorney, Agent, or Firm* — Banner & Witcoff, Ltd.

(57) ABSTRACT

In one aspect, a method of increasing hair growth includes administering to an individual in need thereof a pharmaceutical composition containing a therapeutically effective amount of isomyosmine or a pharmaceutically acceptable salt thereof and a pharmaceutically acceptable vehicle therefor. In another aspect, a method of improving the appearance of hair includes administering to an individual in need thereof a pharmaceutical composition containing a therapeutically effective amount of isomyosmine or a pharmaceutically acceptable salt thereof and a pharmaceutically acceptable vehicle therefor.

15 Claims, 4 Drawing Sheets

METHODS OF INCREASING HAIR GROWTH AND IMPROVING HAIR APPEARANCE

CROSS-REFERENCE TO RELATED APPLICATION

This application is the U.S. national stage of International Application PCT/US17/17641, filed Feb. 13, 2017, which claims priority to U.S. provisional application No. 62/295,618, filed Feb. 16, 2016, the disclosure of which is hereby incorporated by reference in its entirety.

BACKGROUND

Hair growth is a cyclical process which includes a growth stage (anagen), a regression stage (catagen), and a quiescent stage (telogen). During anagen, the hair bulb within the follicle penetrates the dermis and contacts the dermal papilla, triggering division of hair matrix keratinocytes. The new keratinocytes dehydrate and condense to form the hair shaft, which is pushed through the epidermis by newly dividing keratinocytes in the hair root. Hair growth ends in the catagen phase. The hair bulb separates from the dermal papilla, retracts from the dermis, and the follicle shrinks in size. In telogen, the hair remains attached to the follicle but, due to its shallow position in the epidermis, can easily be released from the skin. Normally, the follicle transitions back into anagen phase, during which the hair is pushed out of the follicle by hair newly formed by dividing keratinocytes. Disruption of the hair growth cycle leads to thinning and baldness. On the scalp, hair follicles shrink and shed terminal (long, pigmented) hair. The lost hair is either not replaced by new hair or is replaced by vellus (thin, short, non-pigmented) hair, resulting in the appearance of baldness.

The most common pharmacotherapeutics currently used to treat hair loss are minoxidil and 5-alpha reductase inhibitors, such as finasteride. The precise mechanism by which minoxidil reduces hair loss is unknown; and there is a significant percentage of patients that do not respond to therapy. While finasteride has been shown to slow hair loss in men, the drug is associated with several side effects, including gynecomastia and sexual dysfunction. Both minoxidil and anti-androgens can require several weeks to increase hair count, and must be continued indefinitely on a daily basis to maintain effectiveness. DiColandrea et al. U.S. Pat. No. 8,986,664 describes one alternative approach in which certain monoamine oxidase inhibitors (MAOI) are administered together with a vasodilator to improve hair biology and hair growth.

There remains a need for more effective treatments for improving hair growth and/or for restoring hair color. It would be particularly desirable to development treatments which also improve other qualities of hair associated with aging, such as texture, body, and sheen, which may help provide an overall more youthful appearance.

SUMMARY

In one aspect, a method of increasing hair growth comprises administering to an individual in need thereof a pharmaceutical composition comprising therapeutically effective amount of isomyosmine or a pharmaceutically acceptable salt thereof, and a pharmaceutically acceptable vehicle therefor.

In another aspect, a method of improving the appearance of hair comprises administering to an individual in need thereof a pharmaceutical composition comprising a therapeutically effective amount of isomyosmine or a pharmaceutically acceptable salt thereof, and a pharmaceutically acceptable vehicle therefor. The appearance of hair may be improved by restoring color, increasing sheen, and/or otherwise providing a more youthful appearance or treating attributes of the hair associated with aging.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

Figure 1:
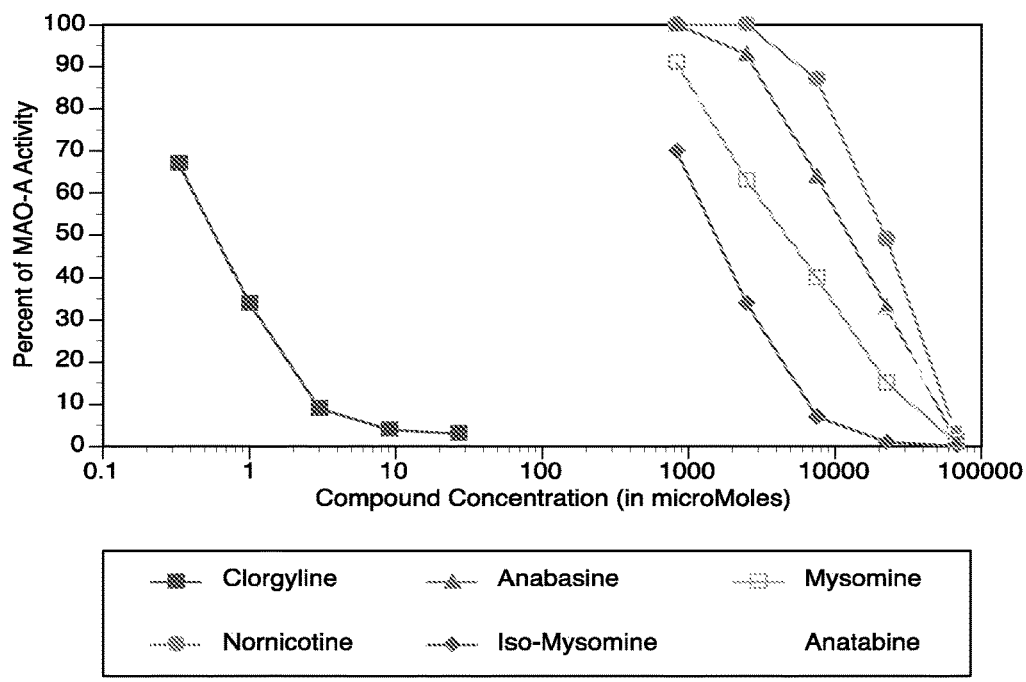
FIG. 1 is a graph showing the ability of isomyosmine, myosmine, anatabine, anabasine, and nomicotine to inhibit the enzymatic activity of MAO-A.

Aspects of the present specification disclose, in part, a pharmaceutical composition. As used herein, the term "pharmaceutically acceptable composition" is synonymous with "pharmaceutical composition" and is one that includes a therapeutically effective concentration of an active ingredient to produce an intended response. A pharmaceutical composition disclosed herein may be useful for medical or veterinary applications. A pharmaceutical composition may be administered to an individual alone, or in combination with other supplementary active ingredients, agents, drugs or hormones. In general, the compositions may be administered by any suitable route, including by not limited to orally, intravenously, transdermally, subcutaneously, topically, parenterally, or a combination thereof. Non-limiting examples of topic formulations include creams, lotions, pastes, shampoos, and the like.

A pharmaceutical composition may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" and "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like;

solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

Isomyosmine

Isomyosmine (3-(3,4-dihydro-2H-pyrrol-2-yl)-pyridine) is a nicotine related alkaloid present in solanecea plants containing nicotine.

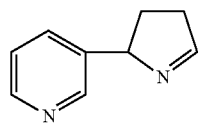 [SMILES: C1=NC(c2cccnc2)CC1]

Isomyosmine may be prepared synthetically using known techniques, and also is commercially available from several chemical suppliers. Isomyosmine has two optical isomers (+/−) owing to an asymmetric carbon atom within its pyrrole ring that joins to the pyridine ring. Unless otherwise clear from context, the term "isomyosmine," as used herein, is inclusive of enantiomeric mixtures (+/−) including racemic mixtures, as well as isolated forms of one or the other enantiomer.

Unless otherwise clear from context, "isomyosmine" as used herein refers to both salt and non-salt forms of isomyosmine. Non-limiting examples of possible salts are described in P. H. Stahl et al., Handbook of Pharmaceutical Salts: Properties, Selection and Use, Weinheim/Zürich:Wiley-VCH/VHCA, 2002, including salts of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

As an alternative to preparing isomyosmine synthetically, isomyosmine can be obtained by extraction from tobacco or other sources in which it occurs naturally. For example, a tobacco extract may be prepared from cured tobacco stems, lamina, or both. In the extraction process, cured tobacco material is extracted with a solvent, typically water, ethanol, steam, or carbon dioxide. The resulting solution contains the soluble components of the tobacco, including isomyosmine. Isomyosmine may be purified from the other components of the tobacco using suitable techniques such as liquid chromatography.

In pharmaceutical applications, an isolated form of isomyosmine generally is used. An "isolated form of isomyosmine," as used herein, refers to isomyosmine that either has been prepared synthetically or has been substantially separated from natural materials in which it occurs. The isolated form of isomyosmine should have a very high purity (including enantiomeric purity in the case where an enantiomer is used). In the case of synthetic isomyosmine, for example, purity refers to the ratio of the weight of isomyosmine to the weight of the end reaction product. In the case of isolating isomyosmine from native material, for example, purity refers to the ratio of the weight of isomyosmine to the total weight of the isomyosmine-containing extract. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

While not wanting to be bound by theory, it is believed that isomyosmine may increase hair growth and/or improve the appearance of the hair by inhibiting monoamine oxidase (MAO), including the MAO-A and MAO-B enzymes, and by blocking the synthesis of hydrogen peroxide ($H_2O_2$) and/or other reactive oxygen species (ROS) in the hair follicles and/or surrounding cells. Increased levels of hydrogen peroxide at the cellular level are associated with the normal aging process and other disorders which may adversely affect the normal hair growth process and pigmentation. Inhibiting the production of ROS such as $H_2O_2$ is postulated to help restore function to mitochondria, thereby increasing hair growth, restoring natural color, and/or improving other characteristics of the appearance of the hair as described herein, e.g., increased sheen, body, etc.

A pharmaceutical composition may include other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Compositions may contain isomyosmine, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt. e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. In some aspects, the therapeutic compound may have anti-inflammatory activity.

Non-limiting examples of other therapeutic compounds include vasodilators, such as minoxidil, apigenin, hydralazine, prostaglandin, and prostacyclin. A significant percentage of subjects do not respond, or are only minimally responsive, to minoxidil treatment alone. For some individuals, co-therapies involving the administration of isomyosmine and a vasodilator, such as minoxidil, may yield improved results over the administration of either component alone. When more than one active agent is administered, the active agents may be present in the same formulation or in two or more different formulations.

A pharmaceutical composition may comprise a therapeutic compound in an amount sufficient to allow customary administration to an individual. For example, a pharmaceutical composition may include, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. The amount of therapeutic compound in a composition may be in the range of, e.g., about 10 mg to about 250 mg, about 10 mg to about 500 mg, about 10 mg to about 750 mg, or about 10 mg to about 1,000 mg.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrilidone (NMP), and diethyl ether.

A pharmaceutical composition disclosed herein may comprise a solvent in an amount sufficient to dissolve a therapeutic compound disclosed herein. In other aspects of this embodiment, a pharmaceutical composition disclosed herein may comprise a solvent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

In one embodiment, a solvent may comprise a pharmaceutically acceptable alcohol. As used herein, the term "alcohol" refers to an organic molecule comprising a hydroxyl functional group (—OH) bonded to a carbon atom, where the carbon atom is saturated. In aspects of this embodiment, the alcohol may be, e.g., a $C_{1-4}$ alcohol, a $C_{2-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. In other aspects of this embodiment, an alcohol may be, e.g., a primary alcohol, a secondary alcohol, or a tertiary alcohol. In other aspects of this embodiment, an alcohol may be, e.g., an acyclic alcohol, a monohydric alcohol, a polyhydric alcohol (also known as a polyol or sugar alcohol), an unsaturated aliphatic alcohol, an alicyclic alcohol, or a combination thereof. Examples of a monohydric alcohol include, without limitation, methanol, ethanol, propanol, butanol, pentanol, and 1-hexadecanol. Examples of a polyhydric alcohol include, without limitation, glycol, glycerol, arabitol, erythritol, xylitol, maltitol, sorbitol (gluctiol), mannitol, inositol, lactitol, galactitol (iditol), and isomalt. Examples of an unsaturated aliphatic alcohol include, without limitation, prop-2-ene-1-ol, 3,7-dimethylocta-2,6-dien-1-ol, and prop-2-in-1-ol. Examples of an alicyclic alcohol include, without limitation, cyclohexane-1,2,3,4,5,6-hexyl and 2-(2-propyl)-5-methyl-cyclohexane-1-ol.

In another embodiment, a solvent may comprise an ester of pharmaceutically acceptable alcohol and an acid. Suitable pharmaceutically acceptable alcohols include the ones disclosed herein. Suitable acids include, without limitation, acetic acid, butaric acid, and formic acid. An ester of an alcohol and an acid include, without limitation, methyl acetate, methyl buterate, methyl formate, ethyl acetate, ethyl buterate, ethyl formate, propyl acetate, propyl buterate, propyl formate, butyl acetate, butyl buterate, butyl formate, isobutyl acetate, isobutyl buterate, isobutyl formate, pentyl acetate, pentyl buterate, pentyl formate, and 1-hexadecyl acetate, 1-hexadecyl buterate, and 1-hexadecyl formate.

In another embodiment, a solvent may comprise a pharmaceutically acceptable polyethylene glycol (PEG) polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a solvent may comprise a pharmaceutically acceptable glyceride. Glycerides comprise a substituted glycerol, where one, two, or all three hydroxyl groups of the glycerol are each esterified using a fatty acid to produce monoglycerides, diglycerides, and triglycerides, respectively. In these compounds, each hydroxyl groups of glycerol may be esterified by different fatty acids. Additionally, glycerides may be acetylated to produce acetylated monoglycerides, acetylated diglycerides, and acetylated triglycerides.

In one embodiment, a solvent may comprise a pharmaceutically acceptable solid solvent. Solid solvents may be useful in the manufacture of a solid dose formulation of a pharmaceutical composition disclosed herein. Typically, a solid solvent is melted in order to dissolve a therapeutic compound. A pharmaceutically acceptable solid solvent includes, without limitation, menthol and PEG polymers described above.

In some aspects, individuals exhibit hair loss or thinning hair which is focal, i.e., limited to a particular region or pattern on the skin, or diffuse. Focal hair loss is most commonly associated with androgenetic alopecia, also known as male-pattern or female-pattern hair loss, which affects the vertex region of the skull. Other types of hair loss include anagen effluvium, telogen effluvium, alopecia greata, and scarring alopecia. While aging is a common cause of hair loss, hair loss or thinning also may be caused by any of a number of medical conditions and environmental insults, such as loose anagen syndrome, tinia capitis, ichthyosiform erythroderma, leprosy, progeria, Siemens syndrome, hyperthyroidism, hypothyroidism, menopause, postpartum, autoimmune disorders, infection (e.g., ringworm, *Demodex folliculorum*), allergic reaction, cosmetic overprocessing, stress, nutritional deficiencies (e.g., resulting from anorexia), poisoning, burns, radiation, compulsive hair pulling or twisting, traction alopecia, and certain medications (e.g., antimitotics, retinoids, ACE inhibitors, lithium, anticonvulsants, anticoagulants, and chemotherapy). In some embodiments, the subject suffers from hair loss that is not associated with hereditary hair loss, such as androgenetic alopecia.

As used herein, the term "treating," refers to reducing or eliminating in an individual a clinical symptom of hair loss or thinning hair, or delaying or preventing in an individual the onset of a clinical symptom thereof. For example, the term "treating" can mean reducing a symptom of a condition characterized by alopecia or related disorder by, e.g., at least 20%, at least 25%, at least 30%, at least 35%, at least 40%, at least 45%, at least 50%, at least 55%, at least 60%, at least 65%, at least 70%, at least 75%, at least 80%, at least 85%°, at least 90%, at least 95%, or more. The actual symptoms associated with hair loss or thinning hair are well known and can be determined by a person of ordinary skill in the art. Those of skill in the art will know the appropriate symptoms or indicators associated with a specific type of hair loss or thinning hair and will know how to determine if an individual is a candidate for treatment as disclosed herein.

In one aspect, the subject is a mammal, such as a male or female human. Alternatively, the subject is a fur- or hair-bearing non-human mammal. In this regard, veterinary and pet care applications also are contemplated wherein the subject is, for example, a canine (such as, but not limited to, a dog or a fox), feline, monkey, chimp, rodent (such as, but not limited to, a hamster, gerbil, rat, chinchilla, degu, or mouse), ferret, guinea pig, skunk, rabbit, bovine, or horse.

Improvements in hair biology are determined using any suitable technique, such as techniques known in the art for evaluating the efficacy of hair care products. For example, the onset of new hair growth may be evaluated by observing changes in hair count or density (number of hairs per predetermined area (e.g., $cm^2$)) or hair weight. Hair count protocols are known in the art and described in, for example, Olsen et al., J. Am. Acad. Dermatol., 47: 377-385 (2002). Methods of evaluating improved hair growth and shine include, but are not limited to, global photograph assessments and subject self-evaluation. Similarly, visual inspection may be used to detect increases in the amount of terminal hair and/or a reduction in vellus hair in a particular region of the body, which also signals improved hair growth. Hair loss also can be evaluated via visual inspection and self-evaluation. Another method of monitoring hair loss involves collecting and counting hair lost during the first morning combing or wash at various time points (e.g., at one week, four weeks, two months, three months, six months, nine months, or one year) during or following treatment. Hair count protocols are further described in, e.g., Wasko et al., Arch. Dermatol., 144(6): 759-762 (2008). Any reduction in the amount of hair lost indicates an improvement in hair biology.

Examination of individual hairs is useful for identifying the hair growth phase of a follicle; anagen hairs comprise a sheath attached to the hair root, while telogen hairs lack a sheath. Other indicators of hair biology, such as hair diameter, curl, breakage, and shine, can be observed microscopically. Tensile strength, elasticity, and breakability also can be evaluated using a dynamometer, while glossmeters are suitable for evaluating hair shine, as described in, e.g., Velasco et al., Br. J. Pharm. Sci., 45(1): 153-(2009). See also Robbins, Chemical and Physical Behavior of Human Hair, 4th Ed., Springer-Verlag, New York (2002). In some cases, hair diameter may be evaluated using a Fiber Dimensional Analysis System (Mitutoyo, Model LSM 5000), or an imaging system as described in Berger et al., British Journal of Dermatology, 149: 354-362 (2003).

In some aspects, the treatments described herein may also prevent or reduce dandruff in a subject, such as dandruff caused by microbe-host interactions (e.g., dandruff caused by *Malassezia* yeasts). Reduction or prevention of dandruff can be determined by any suitable method, such as self-evaluation by the subject, global examination, or observing microbe levels on the affected area (see, e.g., Gemmer et al., J. Clin. Microbiol., 40(9), 3350-3357 (2002)).

In some aspects, the treatments described herein may be effective for improving the appearance of hair. References herein to improving the appearance of hair are particularly inclusive of treating attributes of the hair associated with aging. In some examples, the appearance of the hair may be improved by restoring color, increasing sheen, body, and/or otherwise providing a more youthful appearance. Improvements in the appearance of the hair can be determined by self-evaluation, global examination, and/or other techniques described above.

A therapeutically effective amount of isomyosmine for improving hair growth and/or restoring hair color usually is in the range of about 0.001 mg/kg/day to about 100 mg/kg/day. For example, a therapeutically effective amount may be at least 0.001 mg/kg/day, at least 0.01 mg/kg/day, at least 0.05 mg/kg/day, at least 0.1 mg/kg/day, at least 0.2 mg/kg/day, at least 0.3 mg/kg/day, at least 0.4 mg/kg/day, at least 0.5 mg/kg/day, at least 0.6 mg/kg/day, at least 0.7 mg/kg/day, at least 0.8 mg/kg/day, at least 0.9 mg/kg/day, or at least 1 mg/kg/day. In some cases, a therapeutically effective amount may be in the range of about 0.001 mg/kg/day to about 100 mg/kg/day, about 0.01 mg/kg/day to about 90 mg/kg/day, about 0.05 mg/kg/day to about 80 mg/kg/day, about 0.1 mg/kg/day to about 70 mg/kg/day, about 0.2 mg/kg/day to about 60 mg/kg/day, about 0.3 mg/kg/day to about 50 mg/kg/day, about 0.4 mg/kg/day to about 40 mg/kg/day, about 0.5 mg/kg/day to about 30 mg/kg/day, about 0.6 mg/kg/day to about 20 mg/kg/day, about 0.7 mg/kg/day to about 10 mg/kg/day, or about 0.8 mg/kg/day to about 5 mg/kg/day. As will be appreciated by persons skilled in the art, the appropriate dosing for a particular individual will depend on a number of factors including the individual's metabolism and the severity of the baldness or loss of pigmentation.

Dosing can be single dosage or cumulative (serial dosing), and can be readily determined by one skilled in the art. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

The following examples illustrate but do not limit the scope of the disclosure set forth herein.

Example 1

This example describes experiments for determining monoamine oxidase (MAO) inhibition for isomyosmine and other alkaloids. MAOs are enzymes located on the outer membrane of mitochondria and are involved in the catabolism of monoamine neurotransmitters. There are two well-characterized isoenzymes: MAO-A, which predominantly catabolizes serotonin and norepinephrine, and MAO-B, which preferentially catabolizes benzylamine and phenylethylamine. Dopamine and tyramine are metabolized by both isoforms.

To detect the activity of MAO, a luminescent method (MAO-Glo Assay kit, from Promega, Cat # V1401) was used. In this method, a MAO substrate (a derivative of beetle luciferin provided in the kit) is mixed with the compound to be tested (in this case, myosmine and control compounds). Then, the MAO enzymes (either A or B, purchased separately) are added to the mixture and incubated with the reaction for 1 hour at room temperature. The MAO enzymes, if not inhibited by the test compound, will convert the substrate into methyl ester luciferin. Finally, a luciferin detection reagent (provided by the kit) is added (20 minutes at room temperature) to stop the MAO reaction and convert methyl ester luciferin into D-luciferin. D-luciferin reacts with luciferase to produce a luminescent signal, which is directly proportional to the D-luciferin concentration and thus the MAO activity; the greater the amount of light produced the higher the activity of MAO. The luminescent signal is measured and recorded using a luminometer.

The following materials were obtained from Toronto Research Chemicals, North York, ON: isomyosmine, catalog #1821350; myosmine, catalog # M835000; anabasine, catalog # A637175; and nornicotine, catalog # N756995. Anatabine was obtained from Emerson Resources, Norristown, Pa.

As positive controls for the experiment, clorgyline (a well-characterized potent inhibitor of MAO-A) and deprenyl (a well-characterized potent inhibitor of MAO-B) were used.

Results for MAO-A Activity

When the pure alkaloids isomyosmine, myosmine, anatabine, anabasine, and nornicotine were compared, isomyosmine was the most potent of the five in inhibiting the enzymatic activity of MAO-A (FIG. 1). The way to read this line graph is the following: a 100% activity means that the test compound has no effect on the enzyme; a 0% activity means that the test compound completely kills the enzyme. The more the curve is shifted to the left, the greater the inhibition the test compound exerts on the enzyme. As can be seen in FIG. 1, the curve for isomyosmine is more shifted to the left among the five alkaloids tested. A 2 mM concentration (2,000 micromolar) gives an inhibition of about 50%. The curve for clorgyline, the positive control for the experiment, is greatly shifted leftward.

Results for MAO-B Activity

Figure 2:
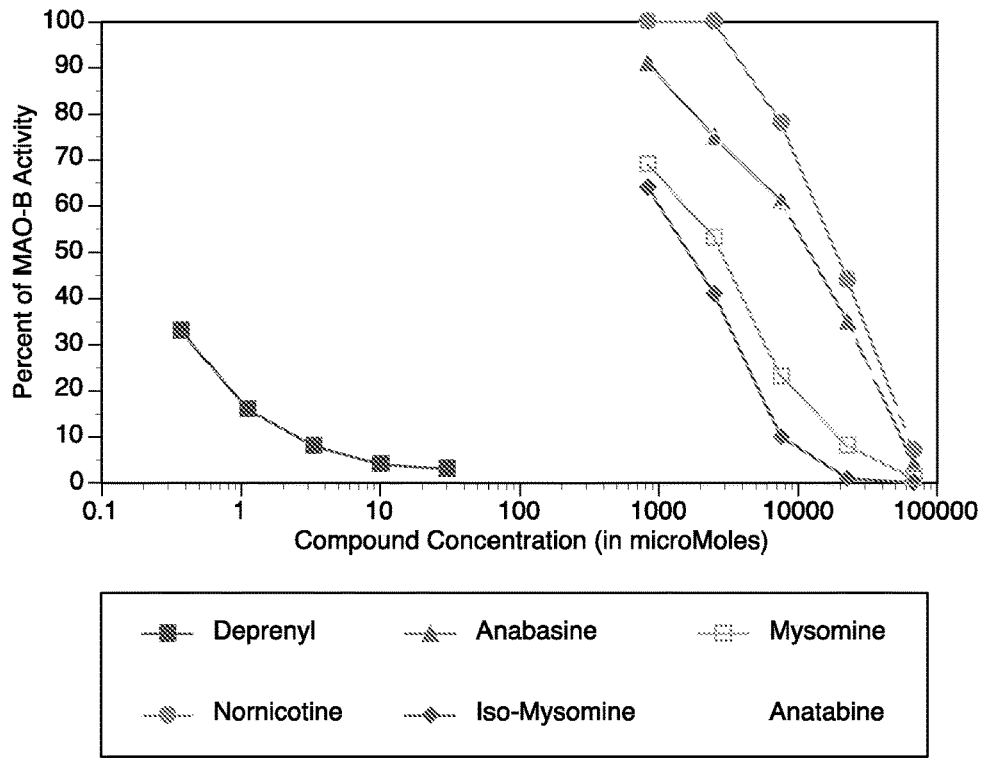
FIG. 2 is a graph showing the ability of isomyosmine, myosmine, anatabine, anabasine, and nomicotine to inhibit the activity of MAO-B.

Similar results were obtained when testing the five pure alkaloids isomyosmine, myosmine, anatabine, anabasine, and nornicotine for the inhibition of MAO-B. Isomyosmine was the most potent among the five alkaloids tested at inhibiting the activity of MAO-B (FIG. 2).

Example 2

Figure 3:
FIG. 3 is a photograph of the scalp of a male subject before treatment.
Figure 4:
FIG. 4 is a photograph of the scalp of the male subject after three weeks of treatment.
Figure 5:
FIG. 5 is a photograph of the scalp of the male subject after 90 days of treatment.

A male aged 60 years and approximately 75 kg in weight was experiencing male-pattern baldness. The individual was orally administered isomyosmine at a dosage of 60 mg/day over the course of three weeks. FIG. 3 is a photograph of the scalp of the individual before treatment. FIG. 4 is a photograph of the scalp of the individual after three weeks of treatment (and a haircut). FIG. 5 is a photograph of the scalp of the individual after 90 days of treatment. As can be seen, the individual experienced significant new growth of healthy, dark-colored hair on the scalp as a result of the treatment.

While particular embodiments have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A method of increasing hair growth comprising administering to an individual in need thereof a pharmaceutical composition comprising a therapeutically effective amount of isomyosmine or a pharmaceutically acceptable salt thereof, and a pharmaceutically acceptable vehicle therefor.

2. The method of claim 1, wherein the pharmaceutical composition is administered orally.

3. The method of claim 1, wherein the pharmaceutical composition is administered topically.

4. The method of claim 1, wherein the therapeutically effective amount ranges from about 0.1 mg/kg/day to about 100 mg/kg/day.

5. The method of claim 1, wherein the therapeutically effective amount ranges from about 0.2 mg/kg/day to about 25 mg/kg/day.

6. The method of claim 1, wherein the therapeutically effective amount ranges from about 0.3 mg/kg/day to about 20 mg/kg/day.

7. The method of claim 1, wherein the therapeutically effective amount ranges from about 0.4 mg/kg/day to about 10 mg/kg/day.

8. The method of claim 1, wherein the therapeutically effective amount ranges from about 0.5 mg/kg/day to about 5 mg/kg/day.

9. A method of improving the appearance of hair comprising administering to an individual in need thereof a pharmaceutical composition comprising a therapeutically effective amount of isomyosmine or a pharmaceutically acceptable salt thereof, and a pharmaceutically acceptable vehicle therefor.

10. The method of claim 9, wherein the pharmaceutical composition is administered orally.

11. The method of claim 9, wherein the pharmaceutical composition is administered topically.

12. The method of claim 9, wherein the therapeutically effective amount ranges from about 0.1 mg/kg/day to about 100 mg/kg/day.

13. The method of claim 9, wherein the therapeutically effective amount ranges from about 0.2 mg/kg/day to about 25 mg/kg/day.

14. The method of claim 9, wherein the therapeutically effective amount ranges from about 0.3 mg/kg/day to about 20 mg/kg/day.

15. The method of claim 9, wherein the appearance of the hair is improved by restoring natural color, increasing sheen, increasing body, or a combination thereof.

* * * * *